United States Patent
Inada et al.

(10) Patent No.: US 6,764,481 B1
(45) Date of Patent: Jul. 20, 2004

(54) PACKAGED OPHTHALMIC PERFUSATE AND CLEANING FLUID BAG

(75) Inventors: Katsuhiro Inada, Kobe (JP); Mitsuhira Nishio, Himeji (JP); Yoshiyuki Kimura, Kakogawa (JP); Junji Kaga, Tokushima (JP); Koichi Muraoka, Naruto (JP); Nobuaki Sumiyoshi, Naruto (JP); Seiichiro Iguchi, Naruto (JP); Hiroaki Yamamoto, Naruto (JP)

(73) Assignees: Otsuka Pharmaceutical Factory, Inc., Tokushima (JP); Senju Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 09/530,507

(22) PCT Filed: Oct. 23, 1998

(86) PCT No.: PCT/JP98/04814

§ 371 (c)(1),
(2), (4) Date: Apr. 27, 2000

(87) PCT Pub. No.: WO99/21527

PCT Pub. Date: May 6, 1999

(30) Foreign Application Priority Data

Oct. 27, 1997 (JP) .............................................. 9/294310
Nov. 14, 1997 (JP) .............................................. 9/313083

(51) Int. Cl.[7] .......................... A61B 19/00; A61K 33/00
(52) U.S. Cl. ...................... 604/408; 604/403; 424/716
(58) Field of Search ........................ 604/403, 408–410; 436/8, 14, 18; 424/715, 716; 210/645, 646

(56) References Cited

U.S. PATENT DOCUMENTS 4,381,776 A * 5/1983 Latham, Jr. ................. 604/317
4,443,432 A * 4/1984 Garabedian et al. ........ 424/127
4,911,933 A * 3/1990 Gilbard ....................... 424/663
5,096,813 A    3/1992 Krumhar et al.
5,500,185 A * 3/1996 Cutler et al. .................. 422/16
5,610,170 A    3/1997 Inoue et al.
5,617,812 A * 4/1997 Balderson et al. .......... 116/206
5,881,879 A * 3/1999 Faict et al. ............... 206/459.1

FOREIGN PATENT DOCUMENTS

| CN | 1097599 A | 1/1995 |
|----|-----------|--------|
| EP | 0 633 013 A1 | 1/1995 |
| EP | 0 639 364 A1 | 2/1995 |
| JP | 58-72515 | 4/1983 |
| WO | WO 93/15402 A1 | 8/1993 |
| WO | WO 97/37628 A1 | 10/1997 |

OTHER PUBLICATIONS

International Search Report.

Supplementary European Search Report.

Patent Abstracts of Japan, vol. 018, No. 381 (c–1226) Jul. 18, 1994, Publication No. 06 105905.

* cited by examiner

Primary Examiner—Angela D. Sykes
Assistant Examiner—Leslie Deak
(74) Attorney, Agent, or Firm—Sughrue Mion, PLLC

(57) ABSTRACT

A packaged ocular irrigating solution bag, which comprises a gas-permeable plastic multiple compartment bag and a gas-impermeable plastic packaging member for packaging the bag and in which an oxiglutatione-containing solution or solid preparation is enclosed in one compartment and a bicarbonate ion solution is enclosed in another compartment and the space between the bag and the packaging member has a carbon dioxide gas atmosphere.

27 Claims, 1 Drawing Sheet

PACKAGED OPHTHALMIC PERFUSATE AND CLEANING FLUID BAG

TECHNICAL FIELD

The present invention relates to a packaged ocular irrigating solution bag. More specifically, the present invention relates to a packaged bag comprising a multiple compartment bag wherein components for preparing a bicarbonate ion- and glutathione- and/or dextrose-containing solution are stably stored and mixed together when used for intraocular or extraocular irrigation or cleaning in an ophthalmic surgery. Especially, the present invention relates to an improved packaged bag thereof which is provided with a pH indicating device whose color changes, thereby permitting a visual inspection of the pH change of the bicarbonate ion-containing solution due to carbon dioxide generation.

BACKGROUND ART

As solutions for intraocular or extraocular irrigation or cleaning in ophthalmic surgeries such as cataract surgery, vitreous surgery and glaucoma surgery, "Opeguard" (produced by Senju Pharmaceutical Co., Ltd. and sold by Takeda Chemical Industries, Ltd.) and BSS PLUS (imported and sold by Santen Pharmaceutical Co., Ltd.) are commercially available at present.

The former "Opeguard" is in a liquid form within a pH range of 7.2–8.2 and comprises dextrose as an active ingredient. This product has a disadvantage of lacking long-term storage stability because dextrose is stable in an acid pH environment.

The latter "BSS PLUS" is in such a form that a solution (10 ml or 20 ml) containing oxiglutatione, dextrose, calcium ion and magnesium ion and a diluent (240 ml or 480 ml) containing bicarbonate ion are separately stored in glass vials, the solution containing oxiglutatione, etc. being transferred into the vial containing the diluent using a syringe having a double ended needle and mixed together before use. This is because it is difficult to stably maintain oxiglutatione and dextrose at pH 7 or above for a long time and because there is a disadvantage that calcium ion and magnesium ion in contact with the diluent for a long period of time cause precipitation.

The above "BSS Plus" can be stably stored for a long period of time but requires transferring procedures as shown below in (1) to (4) and consequently has the disadvantages as shown below in (a) to (f).

(1) A cap is removed from the rubber stopper of the glass bottle containing 10 ml or 20 ml of the oxiglutatione solution, and a cap is removed from the resin needle at one end of the syringe. The rubber stopper of the bottle is pierced by the needle.

(2) Next, a cap is removed from the stainless steel needle at the other end.

(3) An aluminum cover is removed from the glass bottle containing the diluent, and the rubber stopper of the bottle is pierced by the stainless steel needle.

(4) After transferring the oxiglutatione solution into the bottle of the diluent, the two liquids are well mixed.

(a) The above procedure itself is complicated. Especially, the operation of piercing the rubber stopper of the oxiglutatione solution-containing bottle with the resin needle is considerably difficult.

(b) The transferring and mixing of the two liquids take too much time to be responsive to urgent use.

(c) The risk of bacterial contamination at the time of transferring and mixing can not be avoided.

(d) The risk of foreign matter contamination increases if the resin needle is stuck into the rubber stopper of the bottle twice or more.

(e) If the mixing procedure is mistaken, the two liquids are not mixed or the concentration of the resulting solution changes.

(f) There is a possibility that only the diluent is inadvertently administered without mixing with the oxiglutatione solution.

Moreover, not only "Opeguard" and "BSS Plus" but also these types of ocular irrigating solutions are generally in the liquid form, stored in glass vials and adjusted to an alkaline pH range near pH 8 using bicarbonate ion. Therefore, if placed in glass bottles and then sterilized by heating for preservation, the conventional products have a fatal defect that the glass falls in flakes with the lapse of time.

Therefore, there is desired in this industry the development of a new ocular irrigating solution which replaces conventional ocular irrigating solutions and solves all the defects of the conventional solutions.

Bicarbonate ion (hydrogencarbonate ion) used in these types of ocular irrigating solutions is at equilibrium in solution, as represented by the following formula (1):

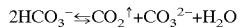

$$2HCO_3^- \leftrightarrows CO_2\uparrow + CO_3^{2-} + H_2O$$

In an open system, the reaction proceeds to the right as the carbon dioxide gas on the right-hand side of formula (1) evaporates, with the result that the bicarbonate ion decreases and the carbonate ion increases. As a result, the pH of the aqueous solution rises progressively.

Healthy human lacrimal fluids are within a pH range of 7.5±0.2 in the arousal state, and at about pH 7.25 in the condition that the eyes are closed for hours. It is necessary to adjust the pH of an ocular irrigating solution to the above-mentioned range as much as possible because the human feels discomfort when it is out of the above pH range, for example, at pH 6 or below or at pH 8 or above. The pH rise deviating from this range must be prevented to the utmost.

Therefore, in order to prevent the time-dependent pH change, ocular irrigating solutions are conventionally contained in glass vials or like sealed containers for preventing evaporation of evolved carbon dioxide gas to thereby maintain the equilibrium essential to the stabilization of bicarbonate ion concentration and solution pH.

However, containers made of glass are easy to be broken, are very heavy and involve difficulties in disposal. In addition to these fatal defects, since the evolution of carbon dioxide gas in the course of sterilization of the ocular irrigating solutions is unavoidable, the risk for an elevation of internal pressure inducing fracture of the glass container is high.

Further, there is another disadvantage. As stated above, it is preferable for bicarbonate ion-containing ocular irrigating solutions to be weak alkaline solutions within a pH range of about 7–8. At such pH, however, if the solutions are placed in glass containers and sterilized by heating for preservation, the glass of the container wall falls in flakes with the lapse of time, making long-term preservation impossible.

An object of the present invention is to overcome all the above-mentioned defects of the prior art and provide a packaged ocular irrigating solution bag which is capable of providing an oxiglutatione- and/or dextrose- and bicarbonate ion-containing ocular irrigating solution in stable condition for a long period of time, most effectively preventing the pH change of the bicarbonate ion-containing solution due to evolution of carbon dioxide gas and providing an unmistakable visual indication of the pH change of the solution.

The present inventors carried out intensive research to achieve the above object and found the following. In a gas-permeable plastic multiple compartment bag, a bicarbonate ion-containing solution is enclosed in one of the compartments and an oxiglutatione- and/or dextrose-containing solution or solid preparation is enclosed in another compartment, followed by sterilization thereof according to a general sterilization method such as autoclave sterilization, hot water immersion sterilization or hot water shower sterilization, or the above pharmaceuticals are aseptically enclosed in the compartments. Then the obtained bag is packed with a gas-impermeable plastic packaging member, and carbon dioxide gas is fed into the space between the bag and the packaging member. In such a case, an ocular irrigating solution can be prepared by bringing the compartments of the bag into communication with each other and mixing the contents of the bag when used, thus enabling stable storage of the ocular irrigating solution, which is one of the objects of the invention.

The present inventor further found that when the multiple compartment plastic bag is packed with a gas-impermeable plastic packaging member and a specific pH indicating device is disposed in the space between the bag and the packaging member, pH change of the bicarbonate ion-containing solution in one of the compartments of the bag can be accurately checked with the eye. The present invention has been accomplished based on these findings.

DISCLOSURE OF INVENTION

The present invention provides a packaged ocular irrigating solution bag, which comprises a gas-permeable plastic multiple compartment bag and a gas-impermeable plastic packaging member for packaging the bag, the bag comprising at least compartment A wherein an oxiglutatione- and/or dextrose-containing solution (hereinafter referred to as "GSSG/GLU solution") or solid preparation (hereinafter referred to as "GSSG/GLU solid preparation") is enclosed, and compartment B wherein a bicarbonate ion-containing solution (hereinafter referred to as "bicarbonate ion solution") is enclosed, and the space between the bag and the packaging member having a carbon dioxide gas atmosphere.

The present invention further provides a packaged ocular irrigating solution bag, which comprises a gas-permeable plastic multiple compartment bag and a gas-impermeable plastic packaging member for packaging the bag, the bag comprising at least compartment A wherein a GSSG/GLU solution or a GSSG/GLU solid preparation is enclosed, and compartment B wherein a bicarbonate ion solution is enclosed, the space between the bag and the packaging member having a carbon dioxide gas atmosphere and being provided with a pH indicating device comprising a gas-permeable plastic packet comprising a bicarbonate ion-containing solution and a pH indicator whose color changes in accordance with the pH change of the solution.

Further, the present invention provides the above packaged ocular irrigating solution bags having the following features:

(1) The packaged ocular irrigating solution bag wherein an oxygen sensor is disposed in the space between the multiple compartment bag and the packaging member.

(2) The packaged ocular irrigating solution bag wherein a carbon dioxide-generating oxygen scavenger is disposed in the space between the multiple compartment bag and the packaging member, thereby establishing a carbon dioxide gas atmosphere.

(3) The packaged ocular irrigating solution bag wherein the GSSG/GLU solution enclosed in compartment A further contains at least one species selected from calcium ion and magnesium ion, preferably containing both ions.

(4) The packaged ocular irrigating solution bag wherein the solution enclosed in compartment A is at pH 2.5–6.5, preferably at pH 3.0–6.0.

(5) The packaged ocular irrigating solution bag wherein the GSSG/GLU solid preparation-enclosed compartment A further contains at least one species selected from calcium salts and magnesium salts, preferably containing both salts.

(6) The packaged ocular irrigating solution bag wherein the solution enclosed in compartment B further contains at least one species selected from calcium ion and magnesium ion, preferably both ions, and contains citrate ion.

(7) The packaged ocular irrigating solution bag wherein the solution enclosed in compartment B is at pH 7.0–9.0, preferably at pH 7.0–8.5.

(8) The packaged ocular irrigating solution bag wherein the multiple compartment bag further comprises compartment C wherein a solution containing at least one species selected from calcium ion and magnesium ion, preferably both ions, (hereinafter referred to as "Ca/Mg solution") is enclosed.

(9) The packaged ocular irrigating solution bag wherein the solution enclosed in compartment C is at pH 3.5–5.5, preferably at pH 4.0–5.0.

(10) The packaged ocular irrigating solution bag wherein the multiple compartment bag further comprises compartment C wherein a solid preparation containing at least one species selected from calcium salts and magnesium salts, preferably both salts, (hereinafter referred to as "Ca/Mg solid preparation") is enclosed.

(11) The packaged ocular irrigating solution bag wherein an ocular irrigating solution is prepared by mixing the contents of the multiple compartment bag so that the resulting solution contains the components in the following permissible range, preferably in the following optimum range, per 1000 ml:

| Component | Permissible range (g) | Optimum range (g) |
| --- | --- | --- |
| Oxiglutatione | 0–0.5 | 0–0.3 |
| Dextrose | 0.4–1.8 | 0.7–1.65 |
| Sodium bicarbonate | 1.5–2.5 | 1.9–2.3 |
| Calcium chloride (as an anhydride) | 0.09–0.17 | 0.1–0.15 |
| Magnesium chloride or magnesium sulfate (as an anhydride) | 0.07–0.18 | 0.08–0.16. |

(12) The packaged ocular irrigating solution bag wherein an ocular irrigating solution is prepared by mixing the contents of the multiple compartment bag so that the resulting solution contains the components within the following permissible range, preferably within the following optimum range, per 1000 ml:

| Component | Permissible range (g) | Optimum range (g) |
| --- | --- | --- |
| Oxiglutatione | 0–0.5 | 0–0.3 |
| Dextrose | 0.4–1.8 | 0.7–1.65 |
| Sodium bicarbonate | 1.5–2.5 | 1.9–2.3 |
| Calcium chloride (as an anhydride) | 0.09–0.17 | 0.1–0.15 |

-continued

| Component | Permissible range (g) | Optimum range (g) |
|---|---|---|
| Magnesium chloride or magnesium sulfate (as an anhydride) | 0.07–0.18 | 0.08–0.16 |
| Sodium citrate (as an anhydride) | 0.4–1.4 | 0.7–1.1. |

(13) The packaged ocular irrigating solution bag wherein the space between the multiple compartment bag and the packaging member has a carbon dioxide gas atmosphere having a carbon dioxide concentration of 0.5–20 v/v %, preferably 1–15 v/v %.

(14) The packaged ocular irrigating solution bag wherein the bicarbonate ion-containing solution in the pH indicating device has a concentration of 0.01–2.0 w/v % and the pH indicator is one selected from the group consisting of cresol red, m-cresol purple, thymol blue and phenolphthalein and has a concentration of 10–2000 ppm.

(15) The packaged ocular irrigating solution bag wherein the bicarbonate ion in the pH indicating device is sodium bicarbonate ion.

Based on the utilization of the multiple compartment bag having at least two compartments A and B, the packaged bag of the invention achieves long-term stabilization of an oxiglutatione-, dextrose- and bicarbonate ion-containing solution.

Based on utilizing a gas-impermeable plastic packaging member and providing the space with carbon dioxide gas, for example by disposing a carbon dioxide-generating oxygen scavenger in the space, the packaged bag of the invention prevents evaporation of carbon dioxide evolved from the bicarbonate ion solution into the atmosphere to thereby securely retain the solution at a constant pH value.

The packaged bag of the invention may contain an oxygen sensor in the space. With this structure, one can easily detect the leakage of carbon dioxide gas from the space and invasion of oxygen into the space upon prolonged storage or due to formation of a pinhole in the packaging member, the resulting pH change and deterioration in the quality of the ocular irrigating solution.

The packaged bag of the invention may contain a specific pH indicating device in the space, in place of the above oxygen sensor. With this structure also, the pH change and deterioration of the ocular irrigating solution upon prolonged storage or due to formation of a pinhole in the packaging member can be easily detected by the naked eye.

Based on the utilization of the specific pH indicating device wherein a bicarbonate ion-containing solution is used as an internal solution, the pH of this internal solution also changes in proportion to the change in pH of the bicarbonate ion solution in the bag in response to the carbon dioxide concentration ($CO_2$ partial pressure) within the space. Therefore, by using a pH indicator capable of sensing a pH change of the internal solution, the pH change of the bicarbonate ion solution in the bag can be visualized with a change in color of the pH indicator.

Further, based on the utilization of a plastic bag, the packaged bag of the invention avoids the risk of fracture or generation of glass flakes, is reduced in weight and can be easily fabricated by the conventional manufacturing technology.

The packaged ocular irrigating solution bag of the invention is now described below in detail. The ocular irrigating solution of the invention is prepared using a GSSG/GLU solution or a GSSG/GLU solid preparation and a bicarbonate ion solution and optionally a Ca/Mg solution or a Ca/Mg solid preparation.

The ion concentrations and salt concentrations indicated in this specification are concentrations of ions and salts (calculated as anhydrides) in the ocular irrigating solution prepared by mixing the contents of the multiple compartment bag, unless otherwise specified.

The GSSG/GLU solution (solution enclosed in compartment A) essentially comprises oxiglutatione and/or dextrose, whereas the bicarbonate ion solution (solution enclosed in compartment B) essentially comprises bicarbonate ion. Each solution may further contain at least one species selected from calcium ion and magnesium ion. Especially when the bicarbonate ion solution further contains at least one species selected from calcium ion and magnesium ion, citrate ion is also added for preventing the precipitation.

It is also possible that at least one species selected from calcium ion and magnesium ion may be formed into a Ca/Mg solution and enclosed in another compartment (compartment C) of the multiple compartment, separately from the GSSG/GLU solution and bicarbonate ion solution.

The proportions of these components may be suitably decided. That is to say, the proportions may be selected from the range that the solution obtained by mixing these solutions will have the same composition as this type of conventional ocular irrigating solution or a slight modification thereof. A typical example is such that the ocular irrigating solution obtained by mixing these solutions has the components within the range mentioned above.

The GSSG/GLU solution, bicarbonate ion solution and Ca/Mg solution may further contain phosphate ion or ion of trace metals such as copper, zinc, etc.

It is preferable for the GSSG/GLU solution to contain sodium ion, potassium ion, chlorine ion or the like by adding sodium chloride, potassium chloride or the like. Sodium chloride is usually added in an amount of about 0.5–0.9 w/v %, preferably about 0.6–0.8 w/v %. Potassium chloride is usually added in an amount of about 0.02–0.05 w/v %, preferably about 0.025–0.045 w/v %. Sodium ion and potassium ion may also be added to the bicarbonate ion solution and the Ca/Mg solution.

The compound added to the bicarbonate ion solution to generate bicarbonate ion may be any of sodium bicarbonate, ammonium hydrogencarbonate, potassium hydrogencarbonate and other hydrogencarbonate, and these are used in the aqueous solution form. Also, sodium carbonate,.potassium carbonate or like carbonate aqueous solutions forming carbonate ion may be used as the bicarbonate ion solution, because bicarbonate ion is generated into the solution in a pH range of the obtained solution. The bicarbonate ion concentrations of these aqueous solutions are not limited specifically but usually selected within a range of about 15–50 mM. This corresponds to a concentration of about 0.1–0.4 w/v % when sodium bicarbonate aqueous solution is used. Most preferably, the sodium bicarbonate aqueous solution has a concentration of about 0.16–0.24 w/v %.

The calcium ion-generating compound and magnesium ion-generating compound, which can be added to the GSSG/GLU solution and the bicarbonate ion solution or constitute a Ca/Mg solution, may be any of those conventionally used in this type of ocular irrigating solution, for example, chlorides or sulfates of calcium or magnesium.

The citrate ion added to the bicarbonate ion solution together with calcium ion and/or magnesium ion has the action of preventing the reaction between bicarbonate ion and calcium ion or magnesium ion coexisting in the obtained solution, thereby preventing the precipitation of calcium carbonate and magnesium carbonate. That is to say, citrate ion forms a chelate with calcium ion or magnesium ion, thereby preventing calcium ion or magnesium ion from directly combining with carbonate ion. For example, citrates such as sodium citrate can be mentioned as compounds having such action. The amount of citrate ion is usually selected within the range of about 0.35–2 w/v %, more preferably about 0.5–1.2 w/v %, calculated as citrates.

In view of the stabilization of bicarbonate ion, the bicarbonate ion solution is preferably adjusted to a pH range of about 7.0–9.0, preferably about 7.0–8.5 using a pH adjusting agent such as sodium hydroxide, hydrochloric acid or the like. The solution may further contain a buffer such as disodium hydrogenphosphate, sodium dihydrogenphosphate, dipotassium hydrogenphosphate, potassium dihydrogenphosphate, sodium acetate, potassium acetate or the like having buffer action, which prevents rapid pH change. The buffer is preferably used at a concentration at which the buffer demonstrates enough buffer capacity when the solutions in the compartments of the multiple compartment bag are mixed. For example, the concentration of disodium hydrogenphosphate is preferably selected from the range of about 0.03–0.06 w/v %, preferably from about 0.035–0.05 w/v %. The concentration of sodium acetate is preferably selected from the range of about 0.02–0.06 w/v %, preferably from about 0.03–0.05 w/v %.

On the other hand, the GSSG/GLU solution is preferably adjusted to a pH range of about 2.5–6.5, preferably about 3.0–6.0 using a pH adjusting agent as mentioned above in order to stably preserve oxiglutatione and/or dextrose in the solution. This solution also may include a buffer such as sodium acetate, potassium acetate or the like having buffer action.

The Ca/Mg solution is usually adjusted to a pH range of about 3.5–5.5, preferably about 4.0–5.0, using a pH adjusting agent as mentioned above in order to securely prevent the precipitation of calcium and/or magnesium. The Ca/Mg solution also may contain a buffer such as sodium acetate, potassium acetate, sodium dihydrogenphosphate, potassium dihydrogenphosphate or the like having buffer action.

According to the present invention, a GSSG/GLU solid preparation may be used in place of the GSSG/GLU solution. It is also possible to use a Ca/Mg solid preparation in place of the Ca/Mg solution.

The GSSG/GLU solid preparation comprises essentially at least one species selected from oxiglutatione and dextrose and may further contain at least one species selected from calcium salts and magnesium salts, preferably both salts. The Ca/Mg solid preparation may be prepared using at least one species selected from calcium salts and magnesium salts, preferably both salts. The calcium salts and the magnesium salts may be any of those conventionally used in this type of ocular irrigating solution. For example, chlorides or sulfates of calcium or magnesium can be mentioned.

The GSSG/GLU solid preparation and the Ca/Mg solid preparation may further contain salts of trace metals such as copper, zinc and the like, sodium salts, potassium salts and phosphates such as sodium chloride, potassium chloride, disodium hydrogenphosphate, sodium dihydrogenphosphate, dipotassium hydrogenphosphate, potassium dihydrogenphosphate and the like. The amounts of these additives may be selected within the range that the ion concentration of the ocular irrigating solution obtained by mixing these compounds, etc. will be within the range mentioned above.

The solid preparations may be prepared in a powder form by mixing the component compounds in a powder form or like generally available form. The mixture of the components may be shaped into fine grains, granules, tablets according to the conventional methods. Alternatively, the components may be dissolved in a suitable solvent such as water and the solution may be lyophilized to give a lyophilized powder.

In the packaged bag of the invention, the gas-permeable plastic multiple compartment bag for enclosing (accommodating, filling) the components (GSSG/GLU solution, GSSG/GLU solid preparation, bicarbonate ion solution, Ca/Mg solution, Ca/Mg solid preparation) of the ocular irrigating solution may be selected from bags made of polyethylene, ethylene-vinyl acetate copolymer, polypropylene, polyvinyl chloride or the like or a mixture thereof in a suitable proportion or laminated ones. There is no particular limitation on the shape, size or thickness of the bag but rectangular forms are generally used. The capacity of the bag is generally within the range of about 20 ml to about 3 litters and the thickness is preferably within the range of about 100–500 $\mu$m.

The above-mentioned bag may be a gas-permeable plastic bag comprising at least two intercommunicable compartments separated from one another by a partition wall. Bags of this type are already known in the field of parenteral infusion. For example, a bag equipped with a closure means for preventing intercommunication of two compartments (e.g. Japanese Examined Patent Publication No. 20550/1988, Japanese Examined Utility Model Publication No. 17474/1988) and a bag whose compartments can be simply brought into intercommunication by pressing the compartments to open the sealing portion therebetween (e.g. Japanese Unexamined Patent Publication Nos. 309263/1988 and 4671/1990). According to the present invention, the bicarbonate ion solution may be enclosed in at least one of the compartments, and the GSSG/GLU solution or the GSSG/GLU solid preparation may be enclosed in at least one of the other compartments.

The term "gas-impermeable" as used in describing the gas-impermeable plastic packaging member for use in the invention does not mean that the particular material is strictly impermeable to gases, but is a relative term meaning that it is less permeable to gases than is the above-mentioned bag for enclosing the ocular irrigating solution (solutions for preparation thereof). Thus, even if the packaging member is made of the same material as that of the above bag, it can be used as the gas-impermeable packaging member only provided it is sufficiently thick. The material that can be used for the gas-impermeable packaging member includes those conventionally used, for example, polyethylene terephthalate (PET), polyethylene naphthalate (PEN), polyvinyl alcohol (PVA), ethylene-vinyl alcohol copolymer (EVOH), polyvinylidene chloride (PVDC), and nylon, such plastic materials carrying a vapor-deposition layer of inorganic material such as silicon oxide, aluminum oxide, etc. on the surface, and multiple-layer films (laminate films) made up of such materials. There is no particular limitation on the shape and size of such packaging members only provided that the gas-permeable plastic bag can be suitably accommodated therein. However, it is necessary that, in shape and size, such a packaging member should provide a sufficient space for accepting a carbon dioxide gas atmosphere after packaging and generally speaking, it is preferably so large as to provide a volume equal to about 1.2–3 times the capacity of the gas-permeable plastic bag.

According to the invention, it is important to establish a carbon dioxide gas atmosphere in the space between the bag and the packaging member.

Referring to the technology for establishing a carbon dioxide gas atmosphere in the space between the bag and the packaging member, a typical process comprises transferring a mixed gas containing carbon dioxide gas, such as a mixture of $CO_2$ gas and air or a mixture of $CO_2$ gas and nitrogen gas, into said space. The carbon dioxide concentration of the mixed gas used in this process is selected according to the kind of ocular irrigating solution to be contained in the plastic bag, particularly its bicarbonate ion concentration and pH. For example, when said solution is an aqueous solution prepared by dissolving 2.1 g of sodium bicarbonate in sterile purified water to make a total of 1 litter, the bicarbonate ion concentration of this aqueous solution is 25 mM and the pH of the solution is 8.2. To maintain these values, the carbon dioxide concentration of the mixed gas atmosphere is preferably set to about 0.5–20%.

The bicarbonate ion concentration and pH of the bicarbonate ion solution for use in the present invention are generally about 15–50 mM and about 7.0–9.0, respectively. Preferably the carbon dioxide partial pressure in said space is generally controlled at about 1 mmHg–250 mmHg and it is preferable to select the percentage of carbon dioxide gas in said mixed gas accordingly. More particularly, when the pH of the bicarbonate ion solution immediately after preparation is within the predetermined range, the carbon dioxide gas to be enclosed in the space can be such that its partial pressure will be substantially equal to the carbon dioxide gas partial pressure of the solution.

An alternative method for establishing a carbon dioxide gas atmosphere in the space defined by said bag and packaging member comprises enclosing a carbon dioxide-generating oxygen scavenger capable of absorbing the oxygen gas in the space and releasing a predetermined proportion relative to the amount of the absorbed oxygen, by volume, of carbon dioxide. As carbon dioxide-generating oxygen scavengers, there can be mentioned "Ageless G" and "Ageless GM", both manufactured by Mitsubishi Gas Chemical Co., and "Keep Fresh Type C" manufactured by Toppan Printing Co., Ltd. These products can be enclosed in the space as they are.

The procedures for filling the bag with the ocular irrigating solution, sterilization, packaging with the packaging member, etc. can all be easily carried out in accordance with usual production methods for injections.

According to a preferred embodiment of the packaged ocular irrigating solution bag of the invention, the space between the multiple compartment bag and the packaging member has a carbon dioxide gas atmosphere and an oxygen sensor is disposed in the space. With the oxygen sensor disposed therein, one can easily detect the leakage of carbon dioxide gas from the space and invasion of oxygen into the space upon prolonged storage or due to formation of a pinhole in the packaging member, and particularly detect the resulting pH change and deterioration in quality of the pharmaceutical preparation, thus securing the safety of the ocular irrigating solution.

It is preferable that the oxygen sensor used reacts only with oxygen gas and changes color, etc. to indicate the presence of oxygen, and does not react with other gas. A typical example of oxygen sensor commercially available is "Ageless Eye CS" manufactured by Mitsubishi Gas Chemical Co., Ltd.

The oxygen sensor can detect the presence of even a comparatively small amount of oxygen. Therefore, when it is used in the present invention, it is preferable to lower the oxygen concentration in the space as much as possible. For example, the oxygen concentration is preferably not higher than about 0.5 v/v %. The means for reducing the concentration can be selected, for example, from a method comprising substituting the air in the space with a mixed gas of carbon dioxide gas and inert gas, and a method further comprising placing and enclosing a suitable oxygen scavenger such as the above-mentioned carbon dioxide-generating oxygen scavenger in the space.

According to another preferred embodiment of the invention, the space between the multiple compartment bag and the packaging member has a carbon dioxide gas atmosphere and is provided with a pH indicating device comprising a gas-permeable plastic packet enclosing a bicarbonate-containing solution and a pH-indicator designed to undergo a change in color in response to a pH change of the solution.

Here, only if the bicarbonate ion is contained, there is no particular limitation on the concentration and composition of the internal solution of the pH indicating device but its bicarbonate ion concentration is preferably selected usually from the range of 0.01–2.0 w/v %.

The pH indicator to be incorporated in the above internal solution of the pH indicating device can be selected from a variety of acid-base indicators which are capable of indicating a pH change of the device internal solution as a color change. Since carbon dioxide gas exists in the space, the pH of the indicating device internal solution is equal to the pH of the bicarbonate ion solution enclosed in the bag. Preferred is an indicator which undergoes a change in color with particularly high sensitivity within the critical pH range of the bicarbonate ion solution. Generally, the critical pH of the bicarbonate ion solution is within the neutral to slightly alkaline range as mentioned above (for example, the specification upper limit for a 7% aqueous solution of sodium bicarbonate is pH 8.6 according to JP XIII and the corresponding carbon dioxide gas fraction is about 19%). The pH of the indicating device internal solution which is proportional to the pH of the bicarbonate ion solution is also within the neutral to slightly alkaline range (e.g. the pH of a 0.28% aqueous solution of sodium bicarbonate is 7.0). Therefore, the above-mentioned pH indicator is preferably one which undergoes a change in color within the slightly alkaline range.

The particularly preferred pH indicator is one selected from substances having the following characteristics, viz. (1) a narrow color change interval, (2) a high intensity of color, (3) a favorable direction of color change (from an inconspicuous color to a conspicuous color), (4) high hygienicity (the substance should be highly safe and not migratory), (5) high stability, with the initial color change property being sustained for an extended time.

As substances having such characteristics, there can be mentioned neutral red, aurin, phenol red, o-cresol red, α-naphtholphthalein, m-cresol purple, orange I, thymol blue, phenolphthalein, etc. Among them, more preferable are phenol red (change from yellow to red at pH 6.8–8.4), o-cresol red (change from yellow to red at pH 7.2–8.8), m-cresol purple (change from yellow to purple at pH 7.6–9.2), thymol blue (change from yellow to blue at pH 8.0–9.6) and phenolphthalein (change from colorless to red at pH 8.3–10).

The concentration of the pH indicator should only be such that its color change can be easily recognized by the naked eye and is preferably selected, for example, from the range of about 10–2000 ppm according to the size of the packet (thickness of the fluid layer) in which the pH indicator is enclosed together with the internal solution.

The packet containing said internal solution and pH indicator can be manufactured by the routine manufacturing technology, and the raw material for this gas-permeable plastic packet may be at least equivalent to the bag described hereinbefore in gas permeability. For example, said packet can be fabricated in a continuous series of forming, filling, and sealing by means of a vertical 3-side sealer, a vertical pillow packaging machine, or a rotary packer. When this manufacturing method is employed, the raw material for the packet is preferably a laminated film in consideration of machine processability. Particularly when the bag is made of polyethylene, the packet is preferably made of a polypropylene (outer layer)—polyethylene (inner layer) laminated film or a poly-4-methyl-1-pentene (outer layer)—polyethylene (inner layer) laminated film.

Regarding the size of the packet and the volume of the internal solution, it should be noted that if the quantity of the internal solution enclosed in the packet is too small, the thickness of the indicating device solution layer will be insufficient to make a visual assessment of the color change difficult. Therefore, the packet size and internal solution volume should be selected in consideration of the geometric relation of the bag and the packaging member as well as the ease of recognition of the color change by the naked eye.

The pH indicating device thus prepared tends to develop turbidity owing to growth of bacteria in the internal solution upon prolonged storage. To prevent or control this clouding problem, it can be sterilized by autoclaving. As an alternative, an antiseptic such as benzalkonium chloride, chlorhexidine gluconate or the like, an antibacterial agent such as nalidixic acid, norfloxacin or the like, or a preservative such as p-hydroxybenzoic esters, benzyl alcohol or the like may be added.

Disposition (enclosing) of the packet in said space can be carried out simply by packaging the bag and the packet together in the packaging member. The disposing position is not critical inasmuch as the packet may be visually recognized from outside the package. In this manner, there can be provided an improved packaged bag permitting a visual assessment of the pH change of the ocular irrigating solution in accordance with the present invention.

The preferred embodiment of the packaged ocular irrigating solution bag of the invention is described with reference to the accompanying drawing (FIG. 1). The packaged bag of the invention comprises a gas-permeable plastic multiple compartment bag 2 separately holding a bicarbonate ion solution and a GSSG/GLU solution (drug solutions, 1 and 1) as divided by a weakly sealed portion 6, a gas-impermeable plastic packaging member 3 for packaging the bag, and a pH indicating device 5 as disposed in a space 4 between the bag and the packaging member, with a carbon dioxide gas atmosphere having been established within the space. Based on the above structure, a visual assessment of the pH change of the bicarbonate ion solution in the bag, which is an object of the invention, is made feasible with the various advantageous effects mentioned hereinbefore.

BRIEF DESCRIPTION OF THE DRAWINGS

In FIG. 1, the reference numeral 1 stands for an ocular irrigating solution, 2 for a gas-permeable plastic multiple compartment bag, 3 for a gas-impermeable plastic packaging member, 4 for a space between said bag 2 and packaging member 3, 5 for a gas-permeable plastic packet (pH indicating device), and 6 for a weakly sealed portion of the gas-permeable plastic multiple compartment bag.

BEST MODE FOR CARRYING OUT THE INVENTION

Figure 1:
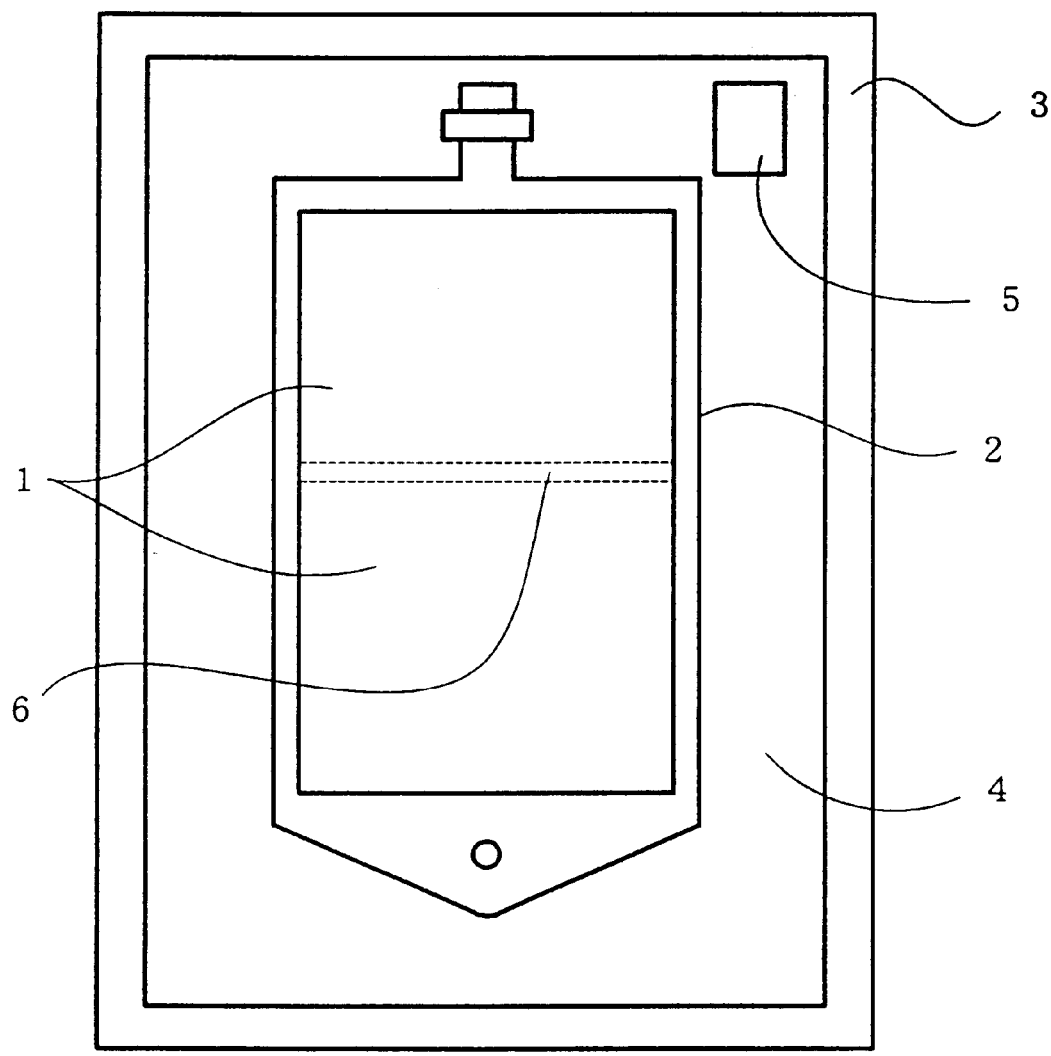
FIG. 1 is a schematic view illustrating a packaged ocular irrigating solution bag according to one embodiment of the invention.

Production examples of pH indicating devices, preparation examples of packaged ocular irrigating solution bags and a test example of the obtained packaged bags are given below to describe the present invention in more detail.

PRODUCTION EXAMPLE 1

In a 0.28% aqueous solution of sodium bicarbonate was dissolved 10 mg of phenol red to make 500 ml (20 w/v ppm). Using a vertical 3-side sealer, 0.5 ml of the above solution was packaged with a polypropylene (outer layer, 20 $\mu$m thick)-polyethylene (inner layer, 30 $\mu$m thick) laminated film to provide a pH indicating device, 30 mm by 15 mm (inside dimensions). This indicating device, freshly prepared, was red-purple (color already developed).

PRODUCTION EXAMPLE 2

In a 0.28% aqueous solution of sodium bicarbonate was dissolved 10 mg of cresol red to make 500 ml (20 w/v ppm). A 0.5 ml portion of this solution was packaged with a polyethylene film (manufactured by Mitsui Petrochemical; 250 $\mu$m thick) to provide a pH indicating device, 40 mm by 20 mm (inside dimensions). Freshly prepared, this indicating device was purple (color already developed).

PRODUCTION EXAMPLE 3

In a 0.28% aqueous solution of sodium bicarbonate was dissolved 10 mg of m-cresol purple to make 500 ml (20 w/v ppm). Using a vertical 3-side sealer, 0.5 ml of the above solution was packaged with a polypropylene (outer layer, 20 $\mu$m thick)-polyethylene (inner layer, 30 $\mu$m thick) laminated film to provide a pH indicating device, 30 mm by 15 mm (inside dimensions). Freshly prepared, this indicating device was purple (color already developed).

PRODUCTION EXAMPLE 4

In a 0.28% aqueous solution of sodium bicarbonate was dissolved 1 g of m-cresol purple to make 50 l (20 w/v ppm). Using Bottlepack 305 (manufactured by Rommelag), forming of a low-density polyethylene packet, filling of a portion of the above solution, and sealing were continuously carried out to provide a pH indicating device, about 20 mm by about 10 mm and about 0.4 mm in wall thickness (fluid volume: about 0.4 ml).

PRODUCTION EXAMPLE 5

In a 0.28% aqueous solution of sodium bicarbonate was dissolved 1 g of m-cresol purple to make 50 l (20 w/v ppm). Using a vertical 3-side sealer, 1 ml of the solution was packaged with an oriented polypropylene (outer layer, 20 $\mu$m thick)-linear low-density polyethylene (inner layer, 60 $\mu$m thick) laminated film to provide a pH indicating device having an external size of 40 mm by 20 mm and an internal size of 30 mm by 12 mm. Until use, this indicating device was stored as packed together with a mixed gas of 10% $CO_2$–90% air in a bag made of nylon (15 $\mu$m thick)-polyvinyl alcohol (18 $\mu$m thick)-low-density polyethylene (60 $\mu$m thick) laminated film.

PRODUCTION EXAMPLE 6

Using a poly-4-methyl-1-pentene (outer layer, 30 $\mu$m thick)-polyethylene (inner layer, 60 $\mu$m thick) laminated film as a packaging member, the procedure of Production Example 5 was otherwise repeated to provide a pH indicating device. Because of the high heat resistance of poly-4-methyl-1-pentene, this product showed improved high-speed sealability for increased productivity. Until use, this pH indicating device was stored together with a mixed gas of 10% $CO_2$–90% air in a bag made of nylon (15 $\mu$m thick)-polyvinyl alcohol (18 $\mu$m thick)-low density polyethylene (60 $\mu$m thick) laminated film.

PRODUCTION EXAMPLE 7

In a 0.28% aqueous solution of sodium bicarbonate was dissolved 1 g of thymol blue to make 50 l (20 w/v ppm). Using a vertical 3-side sealer, a 1 ml portion of the solution was packaged with an oriented polypropylene (outer layer, 30 $\mu$m thick)-linear low-density polyethylene (inner layer, 60 $\mu$m thick) laminated film to provide a pH indicating device having an external size of 40 mm by 20 mm and an internal size of 30 mm by 12 mm. Until use, this indicating device was stored as packed together with a mixed gas of 10% $CO_2$–90% air in a bag made of nylon (15 $\mu$m thick)-polyvinyl alcohol (18 $\mu$m thick)-low-density polyethylene (60 $\mu$m thick) laminated film.

EXAMPLE 1

A polyethylene bag (wall thickness: about 260 $\mu$m) comprising two intercommunicable compartments (compartments A and B: Examples 1–10) or three intercommunicable compartments (compartments A, B and C: Examples 11 and 12) separated from one another by a partition wall was prepared. Solutions, or solution(s) and a solid preparation shown below were separately placed in the compartments and the bag was sealed, followed by sterilization by the hot-water shower method. The bag was enclosed together with the pH indicating device prepared in Production Example 7 and a mixed gas of 10% $CO_2$–90% air in a laminated film bag (secondary packaging member) made of nylon (15 $\mu$m thick)-polyvinyl alcohol (18 $\mu$m thick)-polyethylene (60 $\mu$m thick) laminated film (space volume 400 ml) to provide a packaged ocular irrigating solution bag.

The Packaged Bag of Example 1
(Compartment A) A Solution Having the Following Components

| | |
|---|---|
| Oxiglutatione | 0.09 g |
| Dextrose | 0.46 g |
| Sodium chloride | 3.32 g |
| Potassium chloride | 0.19 g |
| Hydrochloric acid | q.s. |
| Sodium hydroxide | q.s. |
| Sterile purified water | the quantity which makes a total of 150 ml |
| pH | 4.5 |

(Compartment B) A Solution Having the Following Components

| | |
|---|---|
| Sodium bicarbonate | 1.05 g |
| Sodium acetate trihydrate | 0.30 g |
| Sodium citrate dihydrate | 0.50 g |
| Calcium chloride dihydrate | 0.08 g |
| Magnesium chloride hexahydrate | 0.10 g |
| Hydrochloric acid | q.s. |
| Sodium hydroxide | q.s. |
| Sterile purified water | the quantity which makes a total of 350 ml |
| pH | 7.8 |

The Packaged Bag of Example 2
(Compartment A) A Solution Having the Following Components

| | |
|---|---|
| Oxiglutatione | 0.18 g |
| Dextrose | 1.5 g |
| Sodium chloride | 6.7 g |
| Potassium chloride | 0.36 g |
| Hydrochloric acid | q.s. |
| Sodium hydroxide | q.s. |
| Sterile purified water | the quantity which makes a total of 500 ml |
| pH | 3.5 |

(Compartment B) A Solution Having the Following Components

| | |
|---|---|
| Sodium bicarbonate | 2.1 g |
| Sodium acetate trihydrate | 0.5 g |
| Sodium citrate dihydrate | 1.5 g |
| Calcium chloride dihydrate | 0.2 g |
| Magnesium chloride heptahydrate | 0.15 g |
| Hydrochloric acid | q.s. |
| Sodium hydroxide | q.s. |
| Sterile purified water | the quantity which makes a total of 500 ml |
| pH | 7.8 |

The Packaged Bag of Example 3
(Compartment A) A Solution Having the Following Components

| | |
|---|---|
| Dextrose | 0.75 g |
| Sodium chloride | 3.32 g |
| Potassium chloride | 0.18 g |
| Hydrochloric acid | q.s. |
| Sodium hydroxide | q.s. |
| Sterile purified water | the quantity which makes a total of 150 ml |
| pH | 5.0 |

(Compartment B) A Solution Having the Following Components

| | |
|---|---|
| Sodium bicarbonate | 1.05 g |
| Sodium acetate trihydrate | 0.3 g |
| Sodium citrate dihydrate | 0.5 g |
| Calcium chloride dihydrate | 0.09 g |
| Magnesium chloride heptahydrate | 0.15 g |
| Hydrochloric acid | q.s. |
| Sodium hydroxide | q.s. |
| Sterile purified water | the quantity which makes a total of 350 ml |
| pH | 7.2 |

The Packaged Bag of Example 4
(Compartment A) A Solution Having the Following Components

| | |
|---|---|
| Oxiglutatione | 0.09 g |
| Dextrose | 0.46 g |
| Calcium chloride dihydrate | 0.08 g |
| Magnesium chloride hexahydrate | 0.1 g |
| Hydrochloric acid | q.s. |
| Sodium hydroxide | q.s. |
| Sterile purified water | the quantity which makes a total of 150 ml |
| pH | 4.5 |

(Compartment B) A Solution Having the Following Components

| | |
|---|---|
| Sodium bicarbonate | 1.05 g |
| Sodium chloride | 3.57 g |
| Potassium chloride | 0.19 g |
| Disodium hydrogenphosphate dodecahydrate | 0.54 g |
| Hydrochloric acid | q.s. |
| Sodium hydroxide | q.s. |
| Sterile purified water | the quantity which makes a total of 350 ml |
| pH | 7.4 |

The Packaged Bag of Example 5
(Compartment A) A Solution Having the Following Components

| | |
|---|---|
| Dextrose | 0.75 g |
| Calcium chloride dihydrate | 0.09 g |
| Magnesium sulfate heptahydrate | 0.15 g |
| Hydrochloric acid | q.s. |
| Sodium hydroxide | q.s. |
| Sterile purified water | the quantity which makes a total of 150 ml |
| pH | 5.0 |

(Compartment B) A Solution Having the Following Components

| | |
|---|---|
| Sodium hydrogencarbonate | 1.05 g |
| Sodium chloride | 3.55 g |
| Potassium chloride | 0.18 g |
| Disodium hydrogenphosphate dodecahydrate | 0.54 g |
| Hydrochloric acid | q.s. |
| Sodium hydroxide | q.s. |
| Sterile purified water | the quantity which makes a total of 350 ml |
| pH | 7.5 |

The Packaged Bag of Example 6
(Compartment A) A Solution Having the Following Components

| | |
|---|---|
| Oxiglutatione | 0.2 g |
| Dextrose | 1.0 g |
| Calcium chloride dihydrate | 0.16 g |
| Magnesium chloride hexahydrate | 0.2 g |
| Hydrochloric acid | q.s. |
| Sodium hydroxide | q.s. |
| Sterile purified water | the quantity which makes a total of 150 ml |
| pH | 4.5 |

(Compartment B) A Solution Having the Following Components

| | |
|---|---|
| Sodium bicarbonate | 1.9 g |
| Sodium chloride | 7.5 g |
| Potassium chloride | 0.3 g |
| Disodium hydrogenphosphate dodecahydrate | 1.0 g |
| Hydrochloric acid | q.s. |
| Sodium hydroxide | q.s. |
| Sterile purified water | the quantity which makes a total of 500 ml |
| pH | 7.7 |

The Packaged Bag of Example 7
(Compartment A) A Solution Having the Following Components

| | |
|---|---|
| Dextrose | 0.35 g |
| Calcium chloride dihydrate | 0.05 g |
| Magnesium sulfate heptahydrate | 0.09 g |
| Hydrochloric acid | q.s. |
| Sodium hydroxide | q.s. |
| Sterile purified water | the quantity which makes a total of 125 ml |
| pH | 4.5 |

(Compartment B) A Solution Having the Following Components

| | |
|---|---|
| Sodium bicarbonate | 0.47 g |
| Sodium chloride | 1.95 g |
| Potassium chloride | 0.08 g |
| Disodium hydrogenphosphate dodecahydrate | 0.29 g |
| Hydrochloric acid | q.s. |
| Sodium hydroxide | q.s. |
| Sterile purified water | the quantity which makes a total of 125 ml |
| pH | 7.5 |

The Packaged Bag of Example 8
(Compartment A) A Solution Having the Following Components

| | |
|---|---|
| Oxiglutatione | 0.09 g |
| Dextrose | 0.46 g |
| Sodium chloride | 3.57 g |
| Potassium chloride | 0.19 g |
| Calcium chloride dihydrate | 0.08 g |
| Magnesium chloride hexahydrate | 0.1 g |
| Hydrochloric acid | q.s. |
| Sodium hydroxide | q.s. |
| Sterile purified water | the quantity which makes a total of 150 ml |
| pH | 4.5 |

(Compartment B) A Solution Having the Following Components

| Sodium bicarbonate | 1.05 g |
|---|---|
| Disodium hydrogenphosphate dodecahydrate | 0.54 g |
| Hydrochloric acid | q.s. |
| Sodium hydroxide | q.s. |
| Sterile purified water | the quantity which makes a total of 350 ml |
| pH | 7.4 |

The Packaged Bag of Example 9
(Compartment A) A Solution Having the Following Components

| Dextrose | 0.75 g |
|---|---|
| Potassium chloride | 0.18 g |
| Calcium chloride dihydrate | 0.09 g |
| Magnesium sulfate heptahydrate | 0.15 g |
| Hydrochloric acid | q.s. |
| Sodium hydroxide | q.s. |
| Sterile purified water | the quantity which makes a total of 100 ml |
| pH | 4.6 |

(Compartment B) A Solution Having the Following Components

| Sodium bicarbonate | 1.05 g |
|---|---|
| Sodium chloride | 3.55 g |
| Disodium hydrogenphosphate dodecahydrate | 0.54 g |
| Hydrochloric acid | q.s. |
| Sodium hydroxide | q.s. |
| Sterile purified water | the quantity which makes a total of 400 ml |
| pH | 7.5 |

The Packaged Bag of Example 10
(Compartment A) A solid obtained by dissolving the Components shown below in 20 ml of sterile purified water, followed by filtration through a membrane filter haing a pore size of 0.22 μm and lyophlization (the solid being antiseptically enclosed).

| Oxiglutatione | 0.09 g |
|---|---|
| Dextrose | 0.46 g |
| Calcium chloride dihydrate | 0.08 g |
| Magnesium sulfate hexahydrate | 0.10 g |
| Sodium chloride | 3.57 g |
| Potassium chloride | 0.19 g |

(Compartment B) A Solution Having the Following Components

| Sodium bicarbonate | 1.05 g |
|---|---|
| Disodium hydrogenphosphate dodecahydrate | 0.52 g |
| Hydrochloric acid | q.s. |
| Sterile purified water | the quantity which makes a total of 500 ml |
| pH | 7.4 |

The Packaged Bag of Example 11

(Compartment A) A Solution Having the Following Components

| Oxiglutatione | 0.09 g |
|---|---|
| Dextrose | 0.46 g |
| Hydrochloric acid | q.s. |
| Sodium hydroxide | q.s. |
| Sterile purified water | the quantity which makes a total of 100 ml |
| pH | 4.5 |

(Compartment B) A Solution Having the Following Components

| Sodium bicarbonate | 1.05 g |
|---|---|
| Disodium hydrogenphosphate dodecahydrate | 0.52 g |
| Potassium chloride | 0.19 g |
| Hydrochloric acid | q.s. |
| Sodium hydroxide | q.s. |
| Sterile purified water | the quantity which makes a total of 400 ml |
| pH | 7.6 |

(Compartment C) A Solid Obtained by Subjecting the Components Shown Below to Hot Air Sterilization (the Solid Being Antiseptically Enclosed).

| Calcium chloride dihydrate | 0.08 g |
|---|---|
| Magnesium sulfate hexahydrate | 0.10 g |
| Sodium chloride | 3.57 g |

The Packaged Bag of Example 12

(Compartment A) A solid obtained by dissolving the Components shown below in 20 ml of sterile purified water, followed by filtration through a membrane filter haing a pore size of 0.22 μm and lyophlization (the solid being antiseptically enclosed).

| Oxiglutatione | 0.09 g |
|---|---|
| Dextrose | 0.46 g |

(Compartment B) A Solution Having the Following Components

| Sodium bicarbonate | 1.05 g |
|---|---|
| Disodium hydrogenphosphate dodecahydrate | 0.52 g |
| Sodium chloride | 3.57 g |
| Potassium chloride | 0.19 g |
| Hydrochloric acid | q.s. |
| Sodium hydroxide | q.s. |
| Sterile purified water | the quantity which makes a total of 450 ml |
| pH | 7.4 |

(Compartment C) A Solution Having the Following Components

| Calcium chloride dihydrate | 0.08 g |
|---|---|
| Magnesium sulfate hexahydrate | 0.10 g |
| Hydrochloric acid | q.s. |
| Sodium hydroxide | q.s. |
| Sterile purified water | the quantity which makes a total of 50 ml |
| pH | 4.6 |

EXPERIMENT EXAMPLE 1

Using an injection needle (27G, Terumo, Neolus), a pinhole (about 500 μm in major diameter and about 50 μm in minor diameter) was made in the packaging members of the packaged ocular irrigating solution bags of the invention prepared in Examples 1 and 4. The color changes of the pH indicating devices were monitored.

Three days later, both of the pH indicating devices turned green.

INDUSTRIAL APPLICABILITY

According to the present invention, there can be provided a packaged ocular irrigating solution bag wherein an ocular irrigating solution is stably stored in a plastic multiple compartment bag, thus avoiding the fracture of the container or generation of the glass flakes.

What is claimed is:

1. A packaged ocular irrigating solution bag, which comprises a gas-permeable plastic multiple compartment bag and a gas-impermeable plastic packaging member for packaging the bag, the bag comprising at least compartment A comprising oxiglutatione or a mixture of oxiglutatione and dextrose as a solution or solid preparation, and compartment B comprising a bicarbonate ion-containing solution, and a space between the bag and the packaging member having a carbon dioxide gas atmosphere, wherein compartment A and compartment B are intercommunicable with each other such that an ocular irrigation solution is formed when the contents of compartment A and compartment B are mixed.

2. The packaged ocular irrigating solution bag according to claim 1 wherein an oxygen sensor is disposed in the space between the multiple compartment bag and the packaging member.

3. The packaged ocular irrigating solution bag according to claim 1 wherein the carbon dioxide gas atmosphere is established by disposing a carbon dioxide-generating oxygen scavenger in the space.

4. The packaged ocular irrigating solution bag according to claim 1 wherein compartment A comprises oxiglutatione or a mixture of oxiglutatione and dextrose as a solution.

5. The packaged ocular irrigating solution bag according to claim 1 wherein compartment A further comprises at least one species selected from calcium ion and magnesium ion.

6. The packaged ocular irrigating solution bag according to claim 4 or 5 wherein the solution in compartment A is at pH 2.5–6.5.

7. The packaged ocular irrigating solution bag according to claim 6 wherein the solution in compartment A is at pH 3.0–6.0.

8. The packaged ocular irrigating solution bag according to claim 4 wherein the contents of compartment A and compartment B are mixed forming an ocular irrigating solution comprising components in the following range per 1000 ml:

| Oxiglutatione | 0–0.5 g |
|---|---|
| Dextrose | 0.4–1.8 g |
| Sodium bicarbonate | 1.5–2.5 g |
| Calcium chloride (as an anhydride) | 0.09–0.17 g |
| Magnesium chloride or magnesium sulfate (as an anhydride). | 0.07–0.18 g |

9. The packaged ocular irrigating solution bag according to claim 8 wherein the ocular irrigation solution comprises components in the following range per 1000 ml:

| Oxiglutatione | 0–0.3 g |
|---|---|
| Dextrose | 0.7–1.65 g |
| Sodium bicarbonate | 1.9–2.3 g |
| Calcium chloride (as an anhydride) | 0.1–0.15 g |
| Magnesium chloride or magnesium sulfate (as an anhydride) (as an anhydride) | 0.1–0.15 g |
| Magnesium chloride or magnesium sulfate (as an anhydride) | 0.08–0.16 g |
| Sodium citrate (as an anhydride). | 0.7–1.1 g |

10. The packaged ocular irrigating solution bag according to claim 1 wherein compartment A comprises oxiglutatione or a mixture of oxiglutatione and dextrose as a solid preparation.

11. The packaged ocular irrigating solution bag according to claim 10 wherein the solid preparation in compartment A further comprises at least one species selected from calcium salts and magnesium salts.

12. The packaged ocular irrigating solution bag according to claim 1 wherein the solution in compartment B further comprises at least one species selected from calcium ion and magnesium ion; and citrate ion.

13. The packaged ocular irrigating solution bag according to claim 1 wherein the solution in compartment B is at pH 7.0–9.0.

14. The packaged ocular irrigating solution bag according to claim 13 wherein the solution in compartment B is at pH 7.0–8.5.

15. The packaged ocular irrigating solution bag according to any one of claims 12–14 wherein the contents of compartment A and compartment B are mixed forming an ocular irrigating solution comprising components within the following range per 1000 ml:

| Oxiglutatione | 0–0.5 g |
|---|---|
| Dextrose | 0.4–1.8 g |
| Sodium bicarbonate | 1.5–2.5 g |
| Calcium chloride (as an anhydride) | 0.07–0.18 g |
| Magnesium chloride or magnesium sulfate (as an anhydride) | 0.07–0.18 g |
| Sodium citrate (as an anhydride). | 0.4–1.4 g |

16. The package ocular irrigating solution bag according to claim 15 wherein the ocular irrigating solution comprises components within the following range per 1000 ml:

| | |
|---|---|
| Oxiglutatione | 0–0.3 g |
| Dextrose | 0.7–1.65 g |
| Sodium bicarbonate | 1.9–2.3 g |
| Calcium chloride. | |

17. The packaged ocular irrigating solution bag according to claim 1 wherein the multiple compartment bag further comprises compartment C, which comprises a solution comprising at least one species selected from calcium ion and magnesium ion and wherein compartments A, B and C are intercommunicable with each other such that an ocular irrigation solution is formed when the contents of compartment A, B and C are mixed.

18. The packaged ocular irrigating solution bag according to claim 17 wherein the solution in compartment C is at pH 3.5–5.5.

19. The packaged ocular irrigating solution bag according to claim 18 wherein the solution in compartment C is at pH 4.0–5.0.

20. The packaged ocular irrigating solution bag according to claim 1 wherein the space between the multiple compartment bag and the packaging member has a carbon dioxide gas atmosphere having a carbon dioxide concentration of 0.5–20 v/v %.

21. The packaged ocular irrigating solution bag according to claim 20 wherein the carbon dioxide concentration is 1–15 v/v %.

22. The packaged ocular irrigating solution bag according to claim 1 further comprising one or more additional compartments, wherein all compartments of the multiple compartment bag are intercommunicable with each other such that an ocular irrigation solution is formed when the contents of all of the compartments are mixed.

23. A packaged ocular irrigating solution bag, which comprises a gas-permeable plastic multiple compartment bag and a gas-impermeable plastic packaging member for packaging the bag, the bag comprising at least compartment A comprising oxiglutatione or a mixture of oxiglutatione and dextrose as a solution or solid preparation, and compartment B comprising a bicarbonate ion-containing solution, a space between the bag and the packaging member having a carbon dioxide gas atmosphere and pH indicating device comprising a gas-permeable plastic packet containing a bicarbonate ion-containing solution and a pH indicator having the property to undergo a change in color in response to a change in the pH of the solution, wherein compartment A and compartment B are intercommunicable with each other such that an ocular irrigation solution is formed when the contents of compartment A and compartment B are mixed.

24. The packaged ocular irrigating solution bag according to claim 23 wherein the bicarbonate ion-containing solution in the pH indicating device has a concentration of 0.01–2.0 w/v % and the pH indicator is one selected from the group consisting of cresol red, m-cresol purple, thymol blue and phenolphthalein and has a concentration of 10–2000 ppm.

25. The packaged ocular irrigating solution bag according to claim 24 where in the bicarbonate ion in the pH indicating device is sodium bicarbonate ion.

26. The packaged ocular irrigating solution bag according to claim 23 further comprising one or more additional compartments, wherein all compartments of the multiple compartment bag are intercommunicable with each other such that an ocular irrigation solution is formed when the contents of all of the compartments are mixed.

27. The packaged ocular irrigating solution bag according to claim 1 wherein the multiple compartment bag further comprises compartment C, which comprises a solid preparation comprising at least one species selected from calcium salts and magnesium salts and wherein compartments A, B and C are intercommunicable with each other such that an ocular irrigation solution is formed when the contents of compartment A, B and C are mixed.

\* \* \* \* \*